United States Patent [19]
Evans et al.

[11] Patent Number: 5,755,772
[45] Date of Patent: May 26, 1998

[54] RADIALLY EXPANSIBLE VASCULAR PROSTHESIS HAVING REVERSIBLE AND OTHER LOCKING STRUCTURES

[75] Inventors: Michael A. Evans, Palo Alto; Gwendolyn A. Watanabe, Mountain View, both of Calif.

[73] Assignee: Medtronic, Inc., Minneapolis, Minn.

[21] Appl. No.: 638,459

[22] Filed: Apr. 26, 1996

Related U.S. Application Data

[62] Division of Ser. No. 414,995, Mar. 31, 1995.

[51] Int. Cl.$^6$ .................................................. A61F 2/06
[52] U.S. Cl. ........................... 623/1; 623/12; 606/191; 606/198
[58] Field of Search .......................... 623/1, 12; 606/191, 606/198; 604/104, 107

[56] References Cited

U.S. PATENT DOCUMENTS

| | | | |
|---|---|---|---|
| 2,836,181 | 5/1958 | Tapp | 623/1 |
| 3,178,732 | 4/1965 | Stibitz | 5/81 |
| 3,589,356 | 6/1971 | Silverman | 128/1.2 |
| 3,991,767 | 11/1976 | Miller, Jr. et al. | 128/348 |
| 4,441,215 | 4/1984 | Kaster | 3/1.4 |
| 4,470,415 | 9/1984 | Wozniak | 128/334 |
| 4,655,771 | 4/1987 | Wallsten | 623/1 |
| 4,728,328 | 3/1988 | Hughes et al. | 623/12 |
| 4,822,361 | 4/1989 | Okita et al. | 623/12 |
| 4,834,755 | 5/1989 | Silvestrini et al. | 623/13 |
| 4,871,358 | 10/1989 | Gold | 604/271 |
| 4,921,484 | 5/1990 | Hillstead | 604/104 |
| 4,954,126 | 9/1990 | Wallstén | 600/36 |
| 4,976,725 | 12/1990 | Chin et al. | 606/192 |
| 4,994,066 | 2/1991 | Voss | 606/108 |
| 5,037,427 | 8/1991 | Harada et al. | 606/108 |
| 5,045,070 | 9/1991 | Grodecki et al. | 604/271 |
| 5,061,275 | 10/1991 | Wallsten et al. | 623/1 |
| 5,064,435 | 11/1991 | Porter | 623/12 |
| 5,104,399 | 4/1992 | Lazarus | 623/1 |
| 5,127,919 | 7/1992 | Ibrahim et al. | 623/1 |
| 5,171,305 | 12/1992 | Schickling et al. | 604/271 |
| 5,234,457 | 8/1993 | Anderson | 606/198 |
| 5,282,847 | 2/1994 | Trescony et al. | 623/1 |
| 5,443,499 | 8/1995 | Schmitt et al. | 623/1 |
| 5,476,508 | 12/1995 | Amstrup | 623/1 |
| 5,522,881 | 6/1996 | Lentz | 623/1 |
| 5,549,662 | 8/1996 | Fordenbacher | 623/1 |
| 5,556,413 | 9/1996 | Lam | 623/12 |
| 5,575,818 | 11/1996 | Pinchuk | 623/12 |

FOREIGN PATENT DOCUMENTS

| | | |
|---|---|---|
| 0 518 839 A2 | 12/1992 | European Pat. Off. |
| 0 533 511 A1 | 3/1993 | European Pat. Off. |
| 0 682 922 A1 | 4/1994 | European Pat. Off. |
| 0 689 806 A1 | 5/1995 | European Pat. Off. |
| 2714816 | 1/1994 | France |
| WO 88/00813 | 2/1988 | WIPO |
| WO 91/12779 | 9/1991 | WIPO |
| WO 92/11824 | 7/1992 | WIPO |
| WO 94/06372 | 9/1993 | WIPO |
| WO 94/25099 | 11/1994 | WIPO |
| WO 95/01466 | 3/1995 | WIPO |
| WO 96/25124 | 8/1996 | WIPO |

*Primary Examiner*—Paul B. Prebilic
*Attorney, Agent, or Firm*—Townsend and Townsend and Crew LLP

[57] ABSTRACT

A tubular prosthesis is implanted at a target location within a body lumen by transluminally positioning the prosthesis and thereafter radially expanding the prosthesis to conform to an inner wall of the lumen. The prosthesis typically includes a braided tubular body and is typically provided with an everting or other structure for locking the prosthesis in its radially expanded configuration.

32 Claims, 8 Drawing Sheets

RADIALLY EXPANSIBLE VASCULAR PROSTHESIS HAVING REVERSIBLE AND OTHER LOCKING STRUCTURES

This is Division of application Ser. No. 08/414,995 filed Mar. 31, 1995.

BACKGROUND OF THE INVENTION

1. Field of the Invention

The present invention relates generally to methods and apparatus for the endoluminal placement of tubular prostheses, such as grafts, stents, and other structures. More particularly, the present invention relates to a radially expansible stent which preferably includes a braided tubular body and elements for fixing the tubular body in a radially expanded configuration.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well-equipped surgical facilities. Even with the best surgeons and equipment, however, the patients being treated frequently are elderly and weakened from cardiovascular and other diseases, reducing the number of eligible patients. Even for eligible patients, conventional aneurysm repair surgery performed prior to rupture has a relatively high mortality rate, usually from 3% to 10%. Morbidity related to the conventional surgery includes myocardial infarction, renal failure, impotence, paralysis, and other conditions. Additionally, even with successful surgery, recovery can take several weeks and often requires a lengthy hospital stay.

In order to overcome some or all of these drawbacks, endovascular graft placement procedures for the treatment of aneurysms have been proposed. Generally, such endovascular procedures will deliver a radially compressed graft intravascularly to the aneurysm. The graft is then expanded in situ, either by releasing a self-expanding graft or by internally expanding a malleable graft (e.g., using a balloon catheter) to protect the aneurysm. Usually, the vascular graft will comprise both a frame and a liner, where the frame provides the necessary mechanical support and the liner provides the necessary blood barrier.

While highly promising, the endovascular placement of vascular grafts is problematic in several respects. In contrast to surgically implanted grafts, which are sutured in place, endovascularly placed grafts can be difficult to anchor in position. Reliance on the outward spring-force of a self-expanding graft is not always sufficient. Malleable grafts, in contrast, may be easier to initially anchor but may be less able to expand and contract with the blood vessel during the continuous pulse of the patient. While the use of hooks or barbs for anchoring grafts into the blood vessel wall has been proposed, such devices can be traumatic and can loosen from the blood vessel wall over time. As the anchoring of the vascular prosthesis loosens over time, blood can begin to bypass the graft and flow into the region between the graft and the blood vessel wall. Such misdirected blood flow can again expose the patient to risk of aneurysm rupture and its consequences. Additionally, heretofore, it has been difficult to radially reinforce both self-expanding and malleable graft structures to help in maintaining the structures within the blood vessel.

For these reasons, it would be desirable to provide improved endovascular prostheses which can overcome at least some of the difficulties set forth above. In particular, it would be desirable to be able to expand a vascular prosthesis, either by resilient self-expansion or by internal pressurization, and thereafter reinforce the structure to hold the structure in place. It would be even more desirable if such reinforcement did not significantly lessen the flexibility of the prosthesis so that the prosthesis would be able to remain in place and sealing against the blood vessel wall, even over very long periods of time where the prosthesis is exposed to the pulsation of the blood vessel. The vascular and other prostheses of the present invention should be easy to deliver, simple to expand, and permit locking in the expanded configuration with minimum additional effort. In other respects, vascular prostheses of the present invention should have a very simple construction, optionally eliminating the need for a separate liner in addition to the framework. The structure of the vascular prostheses should be capable of employing a wide variety of structural materials, including resilient materials, shape memory alloys, porous materials, biodegradable materials, and should further be useful with designs intended to release drugs from the prosthesis over time.

2. Description of the Background Art

WO 92/11824 describes a braided stent that can be radially expanded by applying an axially compressive force. Braided vascular prostheses are described in U.S. Pat. No. 4,441,215 and WO 88/00813. Vascular prostheses having cuffed or flared ends are described in U.S. Pat. Nos. 4,994,066; 4,728,328; and 3,991,767. Radial expansion of a helical stent by axial shortening with an axial elastic member is described in U.S. Pat. Nos. 5,061,275 and 4,954,126. A self-expanding helical stent including reinforcement filaments, fixation hooks at opposite ends of the stent, or an axial wire securing opposite ends of the stent is described in U.S. Pat. No. 5,064,435. Vascular dilatation catheters having mesh structures which are radially expanded by axial shortening are described in U.S. Pat. No. 4,921,484 and European published application 533 511. Luminal insertion and extraction devices employing eversion mechanisms are described in U.S. Pat. Nos. 5,171,305; 5,045,070; 4,871,358; and 3,589,356 and WO 94/25099. Composite stent structures having permeable or soluble components for drug delivery are described in U.S. Pat. No. 5,234,457 and WO 91/12779. Other patents of interest include U.S. Pat. Nos. 5,127,919; 5,037,427; 4,976,725; 4,822,361; 4,470,415; and 3,178,732; and European published application 518 839.

SUMMARY OF THE INVENTION

The present invention provides methods and apparatus for the transluminal positioning of tubular prostheses at a target location within a body lumen. The tubular prostheses are suitable for a wide variety of therapeutic uses, including stenting of the ureter, urethra, biliary tract, and the like. The devices and methods will also find use in the creation of temporary or long-term lumens, such as the formation of fistulas. The present invention will find its greatest use, however, in the placement of endovascular grafts into blood vessels for the treatment of abdominal and other aneurysms, vascular stenoses, and the like.

In a first particular aspect of the present invention, the tubular prosthesis is positioned at the target location within the body lumen and thereafter radially expanded to conform to an inner surface of the lumen. Radially expansion may be effected in any conventional manner, including the use of a balloon catheter for expanding malleable prostheses, the release of compressed, self-expanding prostheses from suitable delivery catheters, and the like. Once radially expanded, at least a portion of the wall of the tubular prosthesis will be everted in order to fix or lock the radially expanded configuration within the blood vessel. In a preferred aspect, the tubular prosthesis comprises a braided, tubular body which is expanded by applying an axially compressive force. The tubular body is preferably everted at at least one end, and more preferably at both ends, in order to enhance the hoop strength of the expanded structure and lock the structure in its open configuration. Alternatively, the prosthesis may be everted about its midpoint to form a doubled-over structure, or may be everted over a plurality of axially spaced-apart locations to enhance hoop strength at a number of locations.

In a second aspect of the present invention, a braided tubular prosthesis is transluminally positioned at the target location. The braided prosthesis is axially shortened to cause radial expansion, and the expanded configuration is then fixed or locked in place. The preferred method for fixing the radially expanded configuration is by eversion, as described above. Alternatively, the expanded configuration can be fixed by immobilizing the braided tubular prosthesis in other dimension, including length, diameter, and circumference, or by anchoring at least one end of the prosthesis, for example, by using hooks, barbs, or the like. Usually, the prosthesis can be released from its locked or fixed configuration to permit elongation, radial contraction, and removal or repositioning.

In a third aspect of the present invention, a braided tubular prosthesis is introduced to a body lumen, as described above, and the braided tubular prosthesis is axially shortened to effect both radial expansion and a decrease in porosity through a wall of the prosthesis to a final value below about 5000 ml/min./cm². Optionally, after expansion, the braided tubular prosthesis can be fixed by any of the techniques described above.

In yet another aspect of the present invention, a tubular prosthesis comprises a radially expansible tubular body having a first end, second end, and a lumen extending from the first end to the second end. Circumferential structure is provided on the tubular body in order to define at least one fold line to permit eversion of the tubular prosthesis over said fold line. Preferably, the tubular body is a braided structure having both an elongated, narrow diameter configuration and a shortened, large diameter configuration. More preferably, the braided tubular body has a porosity at or above 10,000 ml/min./cm² in the elongated, narrow diameter configuration and a porosity at or below 5000 ml/min./cm² in the shortened, large diameter configuration. The latter porosity is sufficient to permit the tubular prosthesis to act as a graft structure, such as a vascular graft structure, without the need to provide a separate liner.

In a particular aspect of the apparatus of the present invention, the braided tubular body comprises a plurality of helically interwoven elements, where the helical pitch of the elements changes as the body is lengthened and shortened to cause a corresponding decrease or increase in diameter. Usually, the helically interwoven elements are not fixed at cross-over points between the elements, but in some cases may be fixed. The helically woven elements will usually be flat ribbons, typically being composed of metals, organic polymers, porous materials, bioabsorbable materials, radiopaque materials, and the like. While the use of flat ribbon elements can provide the desired porosity characteristics which obviate the need for a separate liner, in some cases it may be desirable to utilize a separate liner to enhance other aspects of the design of the prosthesis.

In the exemplary embodiments, the circumferential structure will comprise a groove, score line, or the like, formed in the surface of the tubular body to provide structural weakness and localize eversion at that location. Alternatively, the circumferential structure may comprise reinforcement over the tubular body to similarly form a preferential fold line. The circumferential structure and resulting fold lines are located wherever it is desired that the tubular body evert when axial pressure is applied. For example, the circumferential structure can be spaced-inward from either end of the prosthesis in order to provide for eversion of both ends of the prosthesis. Alternatively, a single fold line can be provided at or near the middle of the prosthesis in order to permit a single folding over of the device. A further alternative is to provide a plurality of axially spaced-apart circumferential fold lines at a number of locations to enhance hoop strength in a distributed manner over the entire length of the prosthesis. In addition to, or as an alternative to, the eversion structures described above, the prostheses of the present invention can also include hooks, barbs, and other locking structures for holding the expanded tubular body in said expanded configuration. For example, a plurality of hooks can be provided at either or both ends of the tubular body in order to lock each end in its radially expanded configuration. Alternatively, such hooks or barbs could be provided at the everting end(s) in order to lock the eversions into the body after each end has been everted.

In yet another aspect of the present invention, a tubular prosthesis will comprise a radially expansible braided tubular body having means on the body for fixing the radially expanded configuration. The means for fixing the radially expanded configuration can be any of the means described above.

In yet another aspect of the apparatus of the present invention, a tubular prosthesis comprises a braided tubular body which can be axially shortened to effect radial expansion from a first diameter to a second diameter. The braided body has a first end, a second end, and a lumen extending from the first end to the second end. The braid characteristics are chosen so that axial shortening to the second diameter results in a decrease in porosity through the braided body to a final value below about 5000 ml/min./cm². By achieving such a low porosity, the use of a separate liner is not necessary. Other aspects of this embodiment of the tubular prosthesis can be generally as described above for the other embodiments.

DESCRIPTION OF THE SPECIFIC EMBODIMENTS

The present invention provides methods and apparatus for the implanting of tubular prostheses in body lumens. The present invention will find use in the placement of any type of graft or stent in a wide variety of body lumens, including blood vessels, the ureter, the urethra, the biliary tract, and the like. The methods and devices will also find use in the creation of temporary or long-term lumens, such as the formation of fistulas. The preferred use of the present invention, however, is for the percutaneous placement of endovascular grafts and stents for the treatment of diseases of the vasculature, particularly aneurysms, stenoses, and the like.

Tubular prostheses according to the present invention will comprise a tubular body having a radially compressed configuration and a radially expanded configuration. The tubular prosthesis is introduced to a target site within the body lumen with the tubular body in its radially compressed configuration. After proper placement at the target location, the tubular body will be radially expanded, either by releasing the body to permit self-expansion or by applying a force to the body to cause radial expansion, as described in more detail below.

The tubular body of the prosthesis will typically have a length in the range from about 30 mm to 500 mm, preferably from 80 mm to 200 mm, with an expanded diameter in the range from 2 mm to 45 mm, preferably being in the range from 5 mm to 25 mm, and a compressed diameter in the range from 1 mm to 9 mm, preferably from 3.5 mm to 7 mm. These dimensions are particularly suitable for graft structures intended for treating vascular aneurysms.

The tubular body of the prosthesis can have any configuration normally employed for such medical prostheses, including sleeves, lattices, counter-wound helices, braids, and the like. Particular preferred is the use of a braided tubular body comprising a plurality of interwoven elements, such as helically interlaced elements arranged so that axial compression of the body results in radial expansion. Conversely, axial elongation of the element will result in radial compression. The helically interlaced elements in some cases may be fixed at at least some of the cross-over points, but will more usually not be permanently fixed to each other in any way. The interwoven elements are preferably in the form of flat ribbons having a width in the range from 0.025 mm to 2.5 mm, preferably from 0.12 mm to 1.2 mm, and a thickness in the range from 0.025 mm to 1.2 mm, preferably 0.025 mm to 0.5 mm.

It will be appreciated that the interwoven elements of such braided tubular structures will have a variable pitch, with the pitch increasing as the tubular body is axially compressed. For example, in the axially elongated configuration, the pitch of the interwoven elements will typically be in the range from just greater than 0° to 45°, usually from 20° to 35°. Conversely, in the axially compressed configuration, the pitch of the interwoven elements will typically be in the range from 45° to approaching 90°, usually from 50° to 70°.

A particular benefit of the variability in pitch is a decrease in porosity as the braided tubular body is axially compressed. In a preferred aspect of the present invention, the dimension and nature of the interwoven elements, as well as the nature of the variable pitch, will be selected so that the porosity of the wall of the tubular body is sufficiently low when the body is axially compressed that the body will act as a barrier to body fluids. In this way, when used as a vascular graft, it may not be necessary to provide a separate liner or barrier to prevent excessive leakage of blood through the graft. Preferably, the porosity of the axially compressed braided tubular body will be below about 5000 ml/min./cm$^2$, preferably being below about 2000 ml/min./cm$^2$, and more preferably being below about 500 ml/min./cm$^2$. The porosity of the braided tubular body will usually be significantly higher in its axially extended configuration, usually being above 5000 ml/min.cm$^2$, and often being above 10,000 ml/min.cm$^2$. Of course, the porosity in the axially extended configuration is not critical since the braided tubular body of the prosthesis will be implanted in its axially compressed configuration.

The tubular body of the prosthesis can be composed of a wide variety of biologically compatible materials, including metals, organic polymers, and combinations thereof. The materials can further be selected or modified to provide a variety of secondary characteristics, such as shape memory, drug delivery, bioabsorbability, radiopaqueness, hydrophilic swellability, and the like. Frequently, the tubular body will be composed of two or more different materials in order to provide desired characteristics to the body. For example, it may be desirable to fabricate the tubular body both from organic polymers, which can provide flexibility and impermeability, and from metallic elements which can provide self-expansion, resilience, and structural integrity. Such different materials can be incorporated in a variety of ways. For example, different ones of the interwoven elements can be composed of different materials. Alternatively or additionally, the interwoven elements can themselves be composed of two or more materials, particularly when the flat ribbons are composed of multiple individual filaments. Additionally, different materials can be laminated over within the body of the tubular prosthesis to provide for desired properties. For the exemplary braided tubular body, preferred materials of construction include nickel-titanium alloy (Nitinol®), polyester (e.g. polyethylene terephthalate sold under the tradename Dacron®), and polytetrafluoroethylene (PTFE).

The preferred braided tubular body of the prosthesis will usually be radially expanded by applying an axially compressive force, typically using a specially constructed delivery catheter, as described hereinafter. Usually, the length of the braided tubular body may be decreased from about 5% to 95%, usually about 20% to 60%, to effect an increase in diameter (or cross-sectional area) of from about 100% to 2000% (i.e., a ratio of 2:1 to 21:1 starting diameter:final diameter, usually from 100% to 400%. Alternatively, it is possible to construct braided tubular bodies so that they are self-expanding. For example, at least some of the helically interwoven elements of the braid may be formed from a resilient material, usually a metal, such as a shape memory alloy. Such resilient elements will be formed so that they hold the tubular body in its radially expanded configuration when said elements are relaxed, i.e., there is no radially compressive force applied to the tubular body. In this way, the tubular body can be compressed during initial delivery, e.g., held within a tubular delivery catheter or other restraining structure, and released at the target site so that it can self-expand and anchor within the body lumen. It is also possible that the braided tubular body can be formed at least partially from malleable materials so that radially extension can be effected or augmented by internal pressurization, e.g., using a balloon catheter for delivery.

In a preferred aspect of the present invention, a mechanism or structure will be provided on the tubular body of the prosthesis for fixing or locking the prosthesis in its radially expanded configuration. The mechanism or structure will be selected to immobilize the expanded tubular body in at least one dimension, typically length, diameter, or circumference, preferably circumference. Suitable structures for immobilizing the length of the tubular body include axial tethers, axial elements which lock opposite ends of the body in their axially shortened configuration, and the like. Structure which locks the diameter or circumference of the tubular body includes expansible rings, e.g., rings formed from shape memory alloy which expand at body temperature, and the like. Alternatively, discrete latches, barbs, hooks, and other locking mechanisms can be provided for securing either or both ends of the tubular body in their expanded configurations.

A preferred mechanism for fixing the tubular body in its expanded configuration comprises circumferential structure formed on the body to permit eversion of the wall of the body to enhance hoop strength and keep the body radially expanded. The eversion can be either inward or outward, and preferably will occur along a fold line defined by the circumferential structure. At least one such fold line will be provided, usually at least two fold lines, and optionally three or more fold lines will be spaced axially apart along the tubular body. A preferred configuration includes two fold lines spaced axially inward from each end of the tubular prosthesis. The circumferential structure usually comprises a groove or other structural weakening formed in the tubular body so that when axially compressed the body folds over the fold line to create the desired eversion. Alternatively, the structure could provide and reinforcement structure for strengthening of the tubular body along the desired fold line.

The tubular prosthesis of the present invention will be delivered to the intraluminal target site using a suitable delivery system selected depending on the mode of expansion for the prosthesis. For example, radial self-expanding prosthesis can be delivered by a catheter which constrains the prosthesis in its radially pressed configuration. The system will be adapted to release the prosthesis at the target location, allowing it to self-expand and anchor within the lumen. The delivery system will preferably also include means for everting or otherwise fixing the prosthesis in its radially expanded configuration.

Malleable prosthesis will typically be delivered using a balloon catheter which can open the body of the prosthesis at the target location. Again, the balloon catheter will usually be provided with a mechanism for locking the prosthesis in its expanded configuration after balloon expansion.

In a preferred aspect of the present invention, the prosthesis has a braided tubular body which is expanded by axial compression, as described above. The catheter delivery system will hold the prosthesis in its axially elongated configuration during the initial steps of introduction to the body lumen. After the prosthesis has reached its target location, the delivery system will be actuated to axially compress the prosthesis, typically by drawing together a pair of anchor members which hold the prosthesis therebetween. The anchor members are able to directly apply the axially compressive force to radially expand the prosthesis. Preferably, the anchor members will also inwardly evert opposite ends of the prosthesis to fix the body in its radially expanded configuration, as described in more detail hereinafter.

Figure 1:
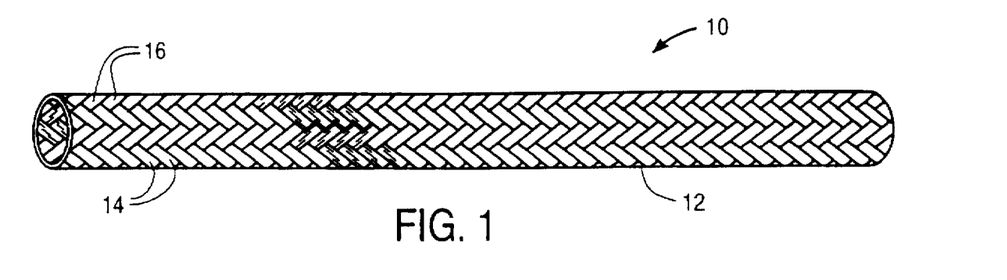
FIG. 1 is a perspective view of a tubular prosthesis comprising a braided tubular body constructed in accordance with the principles of the present invention, shown in its axially extended, radially compressed configuration.
Figure 2:
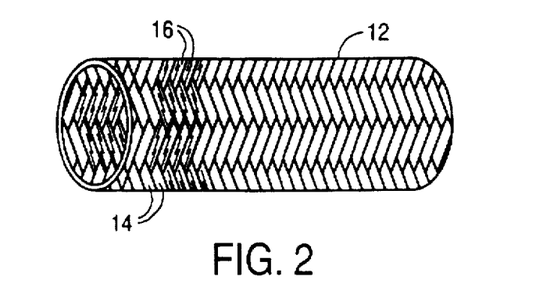
FIG. 2 is a perspective view of the tubular prosthesis of FIG. 1, shown in its axially compressed, radially expanded configuration.

Referring now to FIGS. 1 and 2, an exemplary tubular prosthesis 10 comprises a braided tubular body 12 including a plurality of helically interwoven elements 14 and 16. The helically interwoven elements 14 and 16 are counter-wound with respect to each other and overlap to form the desired axially compressible structure. The helical elements 14 and 16 are in the preferred form of flat ribbons and are not fixed together at cross-over points (except at or near each end where the ribbons are fastened together to prevent unravelling). The tubular prosthesis 10 is shown with the braided tubular body 12 in its elongated, radially compressed configuration in FIG. 1 and in its axially shortened, radially expanded configuration in FIG. 2. As discussed previously, transition between the elongated configuration of FIG. 1 and axially compressed configuration of FIG. 2 can be achieved in a number of way, including self-expansion, expansion by application of internal pressure, or preferably by direct application of an axially compressive force, as described in more detail in connection with FIGS. 13A–13D below.

Figure 3:
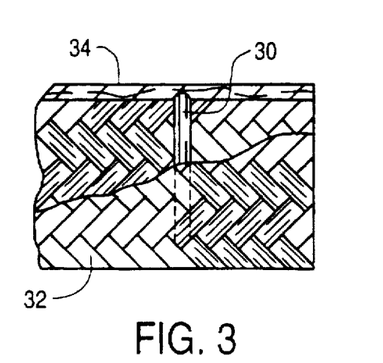
FIG. 3 illustrates one end of a braided tubular prosthesis of the type illustrated in FIGS. 1 and 2, having circumferential structure in the form of a groove circumscribing the tubular body near one end to define a fold line for everting the tubular body to lock the body in its radially expanded configuration.
Figure 4:
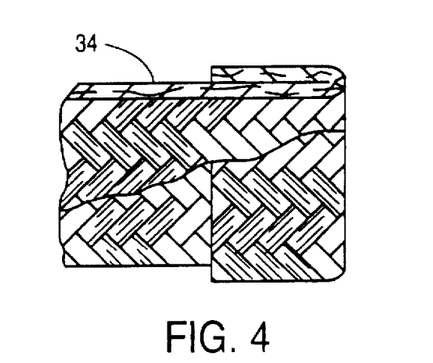
FIG. 4 is a view similar to FIG. 3, showing the end of the tubular body in an outwardly everted configuration.
Figure 5:
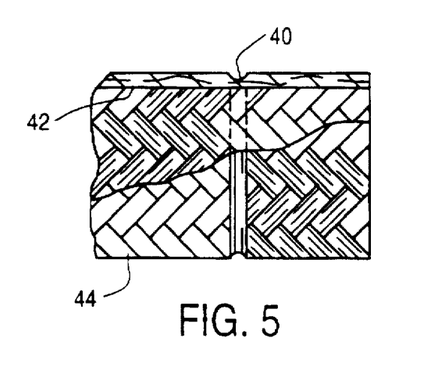
FIG. 5 is a view similar to FIG. 3, showing the circumscribing groove formed on an inner surface of the tubular body.
Figure 6:
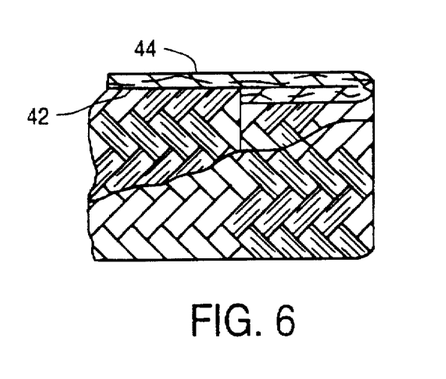
FIG. 6 is a view similar to FIG. 4, showing the end of the tubular body in an inwardly everted configuration.

The tubular prosthesis 10 will preferably include circumferential structure for locking the braided tubular body 12 in its radially expanded configuration. The most preferred circumferential structure is a circumferential groove which defines a fold line or "hinge" for forming an eversion in the radially expanded tubular body, as shown in FIGS. 3–6. In FIG. 3, a fold line 30 in the form of a circumferential groove is formed on an interior surface near one end of a radially expanded braided tubular body 32. The fold line 30 permits the end of the tubular body 32 to be everted outwardly over the exterior surface 34 of the tubular body 32, as illustrated in FIG. 4. A particular technique effecting such an eversion is described in more detail in connection with FIGS. 13A–13D hereinafter. In FIG. 5, a circumferential groove 40 is formed on the exterior surface 42 of a braided tubular body 44. The groove 40 permits an inward eversion of the distal end of the tubular body 44, as shown in FIG. 6. Preferably, the circumferential grooves 30 or 40 will be formed at least at each end of the braided tubular prosthesis so that both ends can be everted to fix the expanded conformation of the prosthesis.

Figure 7:
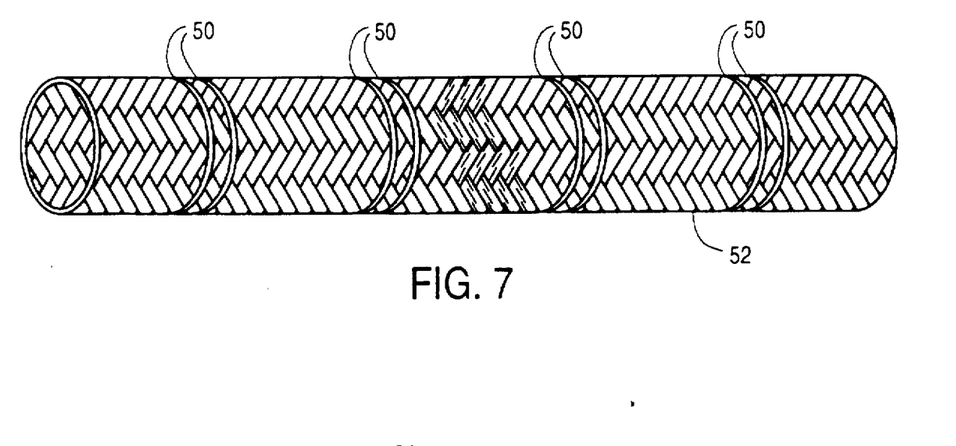
FIG. 7 illustrates an alternative embodiment of the tubular prosthesis of the present invention, wherein the circumferential structure for defining the eversion points comprises a plurality of paired circumscribing grooves which define overlapping fold lines.
Figure 8:
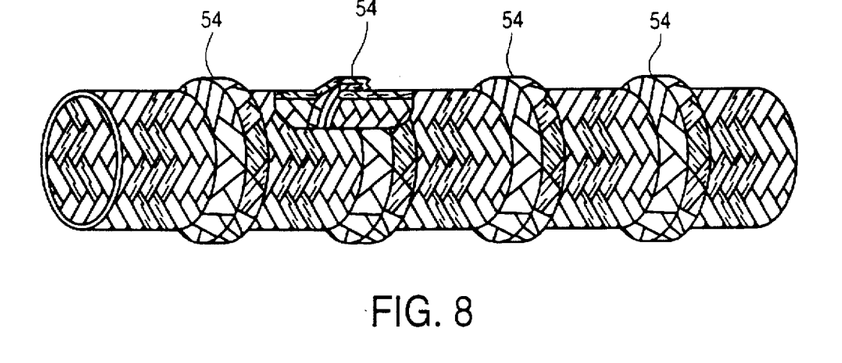
FIG. 8 illustrates the tubular prosthesis of FIG. 7, shown in its fully everted configuration.

Circumferential structure comprising a plurality of closely spaced-apart circumferential grooves is illustrated in FIGS. 7 and 8. Individual grooves in each groove pair 50 are spaced-apart by a short distance, typically from 1 mm to 10 mm, with adjacent pairs of grooves being spaced-apart by a greater distance, typically 10 mm to 100 mm. By applying an axially compressive force to the braided tubular prosthesis 52, a plurality of eversions 54 can be formed in the prosthesis body 52, as illustrated in FIG. 8.

Figure 9:
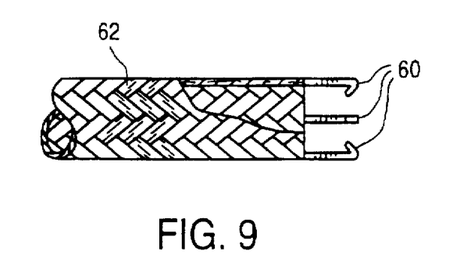
FIG. 9 illustrates an alternative circumferential structure for locking a braided tubular prosthesis in its radially expanded configuration, comprising a plurality of hooks.
Figure 10:
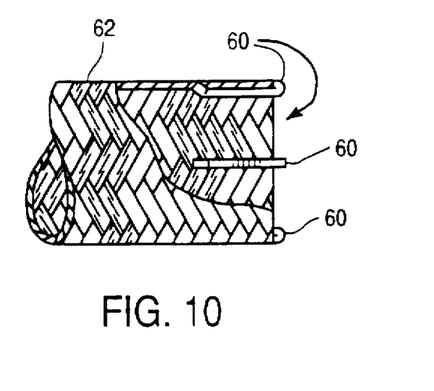
FIG. 10 illustrates the structure of FIG. 9, showing the hooks locking the tubular prosthesis in its radially expanded configuration.

An alternative locking mechanism for fixing and braided tubular prosthesis in its radially expanded configuration is illustrated in FIGS. 9 and 10. The locking mechanism comprises a plurality of individual hooks 60 formed at each end of a braided tubular prosthesis 62. The hooks extend axially outward from the prosthesis when the prosthesis is in its radially collapsed, narrow-diameter configuration, as illustrated in FIG. 9. After expansion of the prosthesis 62, as illustrated in FIG. 10, the hooks may be turned axially inward to lock the terminal portion of the prosthesis in its radially expanded configuration. It will be appreciated that a variety of other hooks, barbs, or other locking mechanism, could be provided at each end of the tubular prosthesis to immobilize that portion of the prosthesis in the radially expanded configuration.

Figure 11:
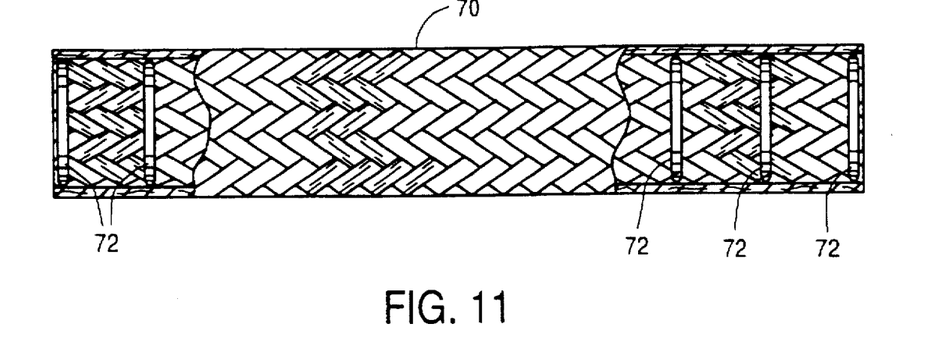
FIG. 11 illustrates another alternative embodiment of the circumferential structure for locking the tubular prosthesis in its radially expanded configuration, comprising a plurality of expansible rings.

Yet another mechanism for locking a braided tubular prosthesis 70 in a radially expanded configuration is illustrated in FIG. 11. There, a plurality of expandable rings 72 are provided over the interior lumen surface of the prosthesis 70. The rings are initially in a small-diameter configuration, and the rings expand and lock into an enlarged diameter configuration after the tubular body of the prosthesis 70 is expanded. For example, the ring 72 can be formed of a heat memory alloy which expands upon exposure to body temperature.

Figure 12:
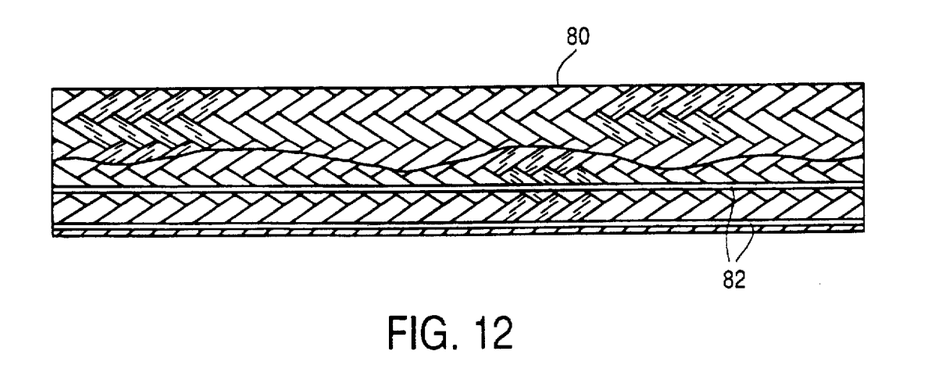
FIG. 12 illustrates yet another embodiment of the circumferential structure, comprising a plurality of axial elements which lock the tubular prosthesis in its axially shortened configuration.

Yet another mechanism for maintaining a tubular prosthesis 80 in a radially expanded configuration is illustrated in FIG. 12. In that embodiment, a plurality of axial elements 82 are provided over the interior lumen surface of the prosthesis 80. The axial elements 82 serve to anchor the opposite ends of the prosthesis in their axially compressed configuration so that the expanded radial configuration is maintained. For example, the axial elements 82 could be composed of a heat memory alloy which assumes an axially shortened configuration upon exposure to body temperature. Alternatively, axial elements 82 could have a fixed length with hooks or detents at each end for capturing opposite ends of the prosthesis 80 after the prosthesis has been suitably shortened. A wide variety of other suitable mechanisms for anchoring a braided tubular prosthesis in the radially expanded configuration would be available.

Figure 13A:
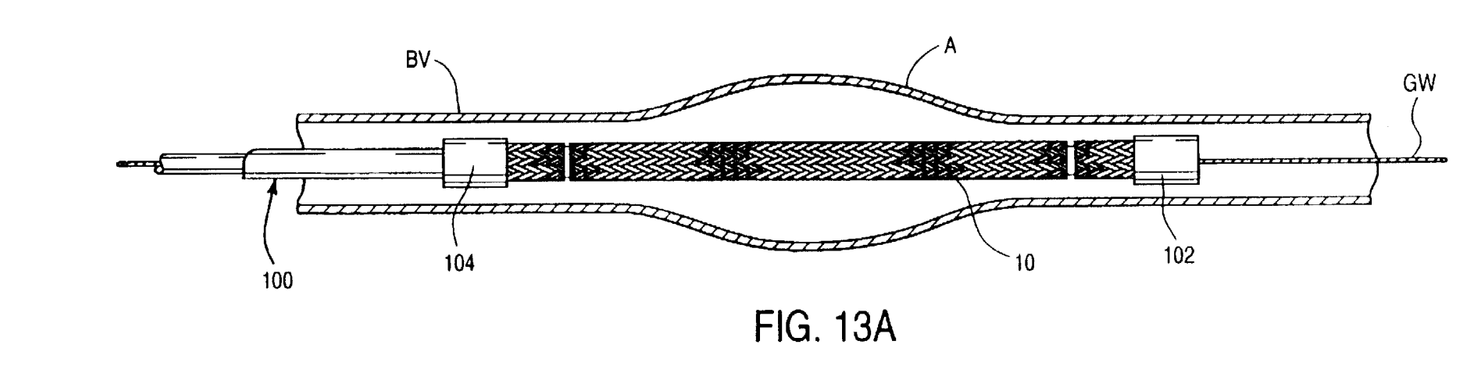
FIGS. 13A–13D illustrate the transluminal placement of a braided tubular prosthesis according to the method of the present invention.
Figure 13B:
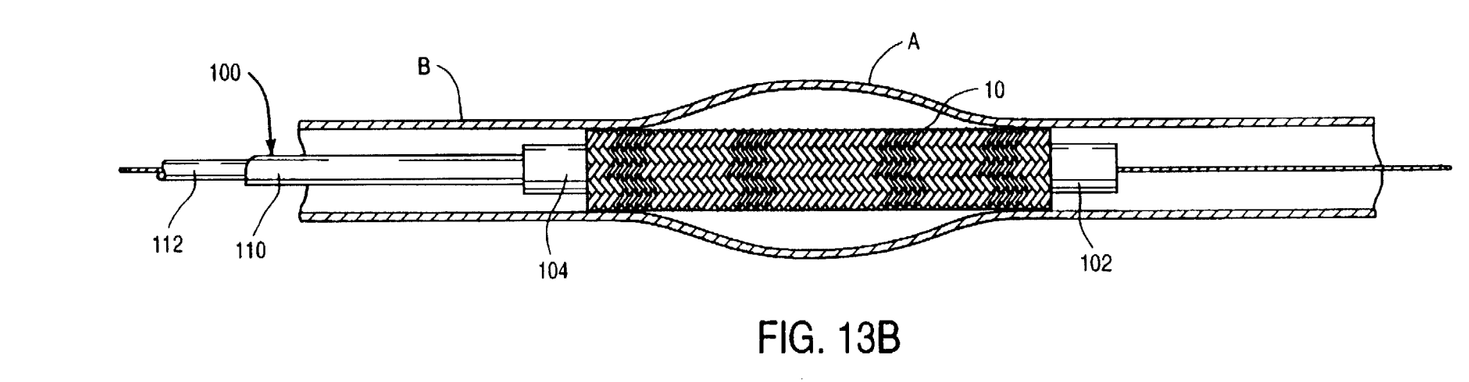
Figure 13C:
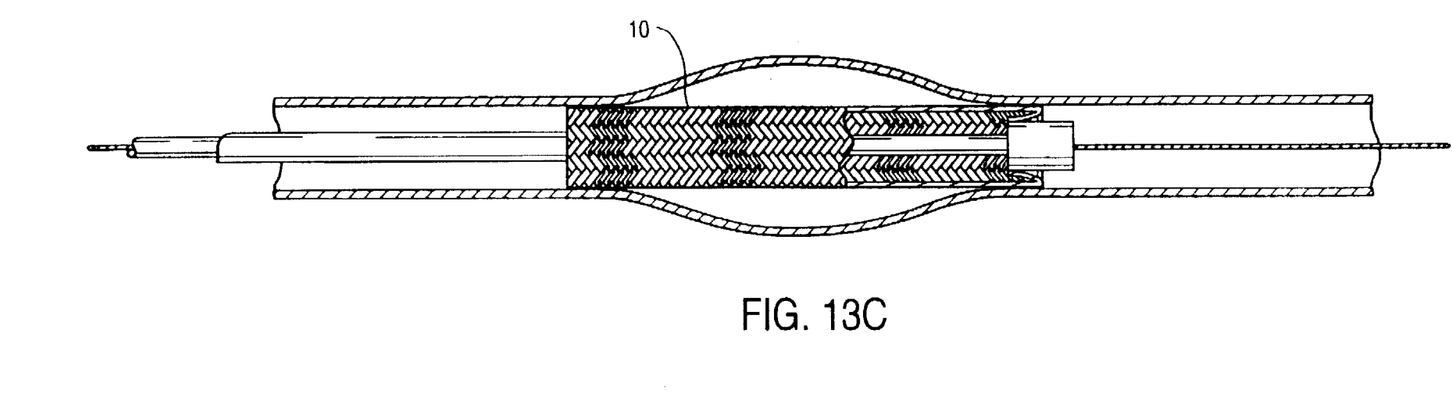
Figure 13D:
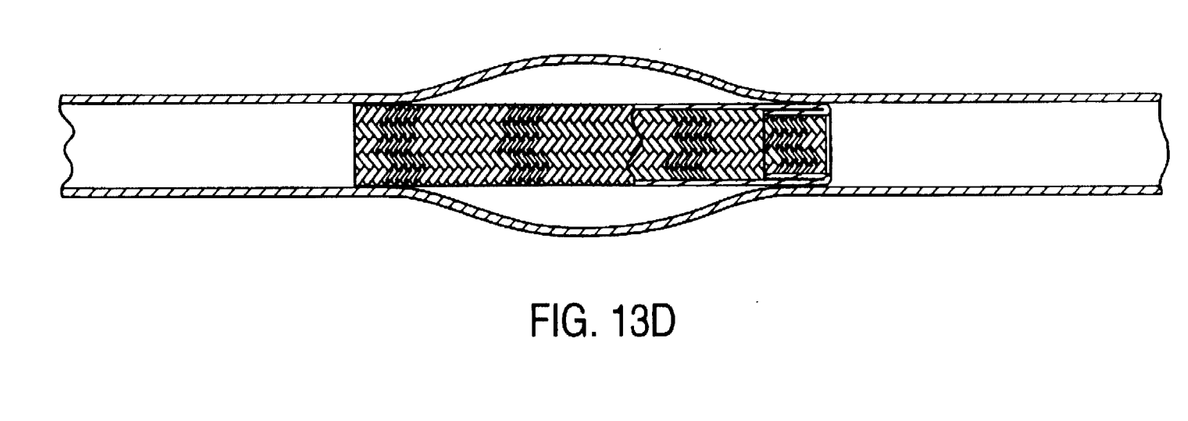

Referring now to FIGS. 13A–13D, the braided tubular prosthesis of FIGS. 1–5, and 6 may be introduced to a target aneurysm A in a blood vessel BV using a catheter 100 having a distal retainer member 102 and a proximal retainer 104. Opposite ends of the braided tubular prosthesis 10 are initially captured within the retainers 102 and 104, respectively, while the catheter is introduced over a guide wire GW. After proper placement at the aneurysm A, the retainer elements 102 and 104 can be axially compressed by drawing together an outer tube 110 and inner tube 112 of the catheter 100. Such axial compression causes radial expansion of the prosthesis 10, as illustrated in FIG. 13B. By continuing to draw the retainer members 102 and 104 together, as illustrated in FIG. 13C, the distal ends of the prosthesis 10 can be everted inwardly. After fully drawing the retainers 102 and 104 together, the distal ends of the prosthesis 10 will be fully everted, as shown in FIG. 13D. Such eversion greatly enhances the hoop strength at each end of the prosthesis and helps anchor the prosthesis in place at the target location.

Figure 14:
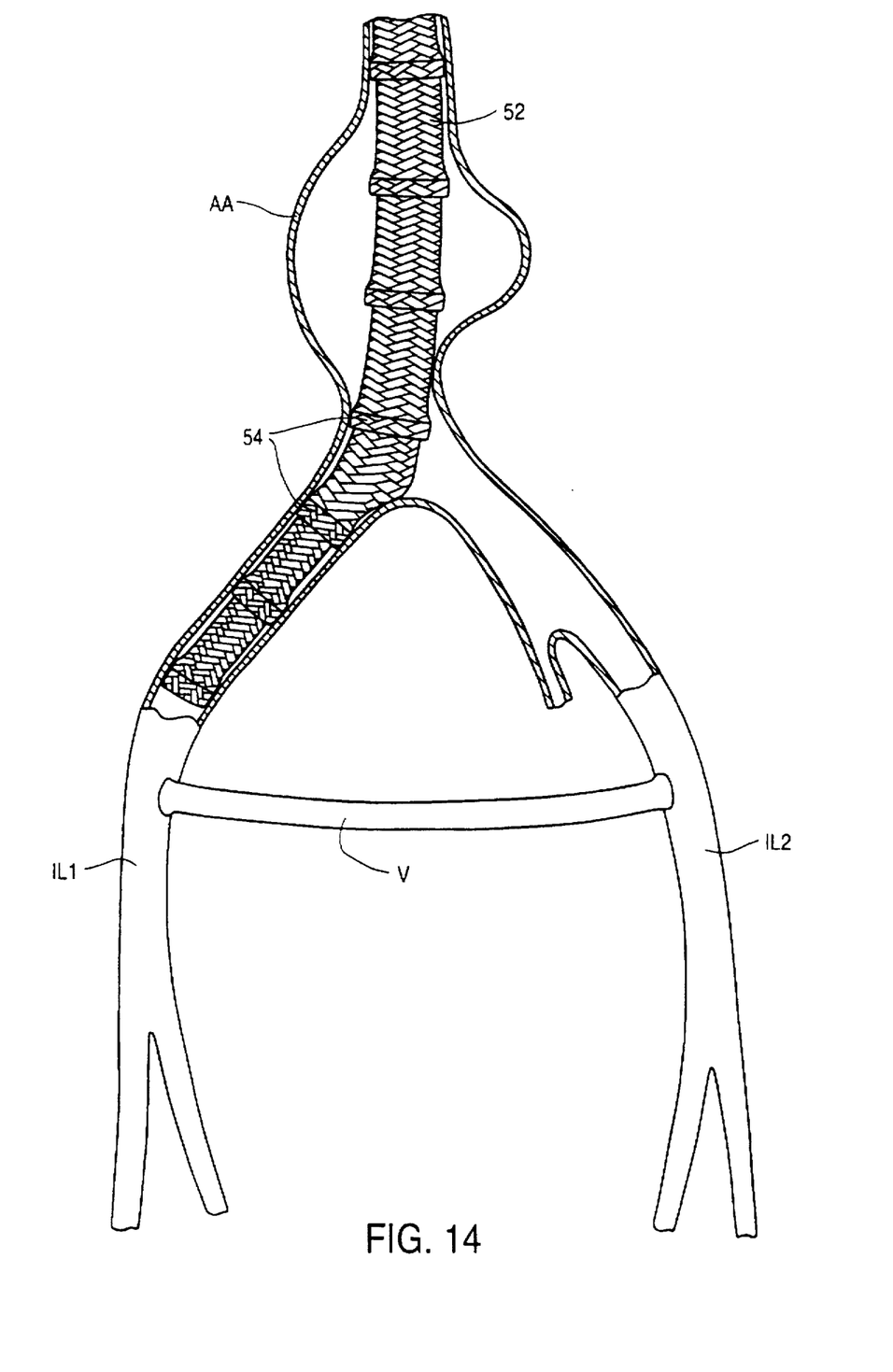
FIGS. 14–16 illustrate use of a tubular prosthesis of the type shown in FIGS. 7 and 8 for treatment of an abdominal aortic aneurysm.
Figure 15:
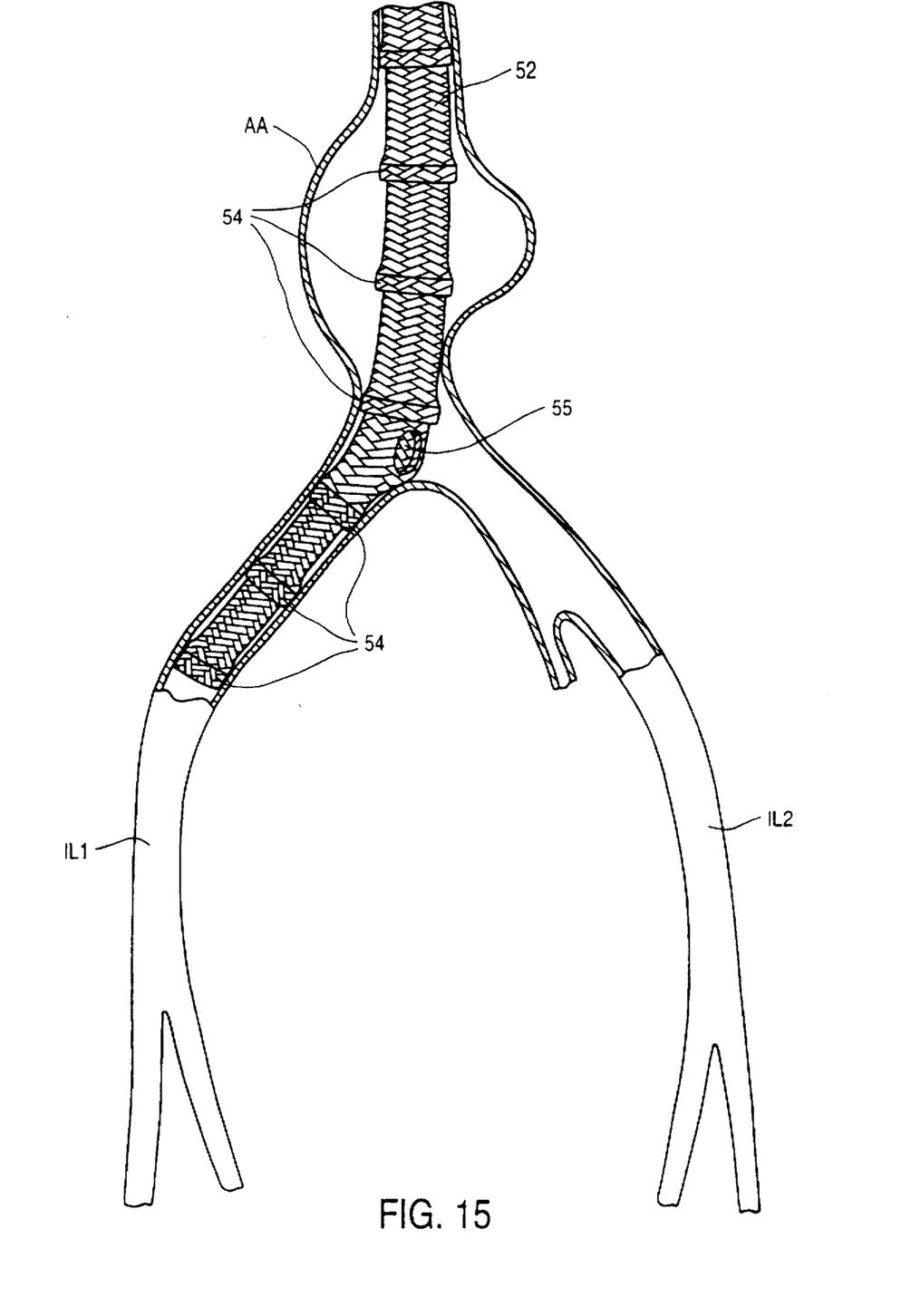
Figure 16:
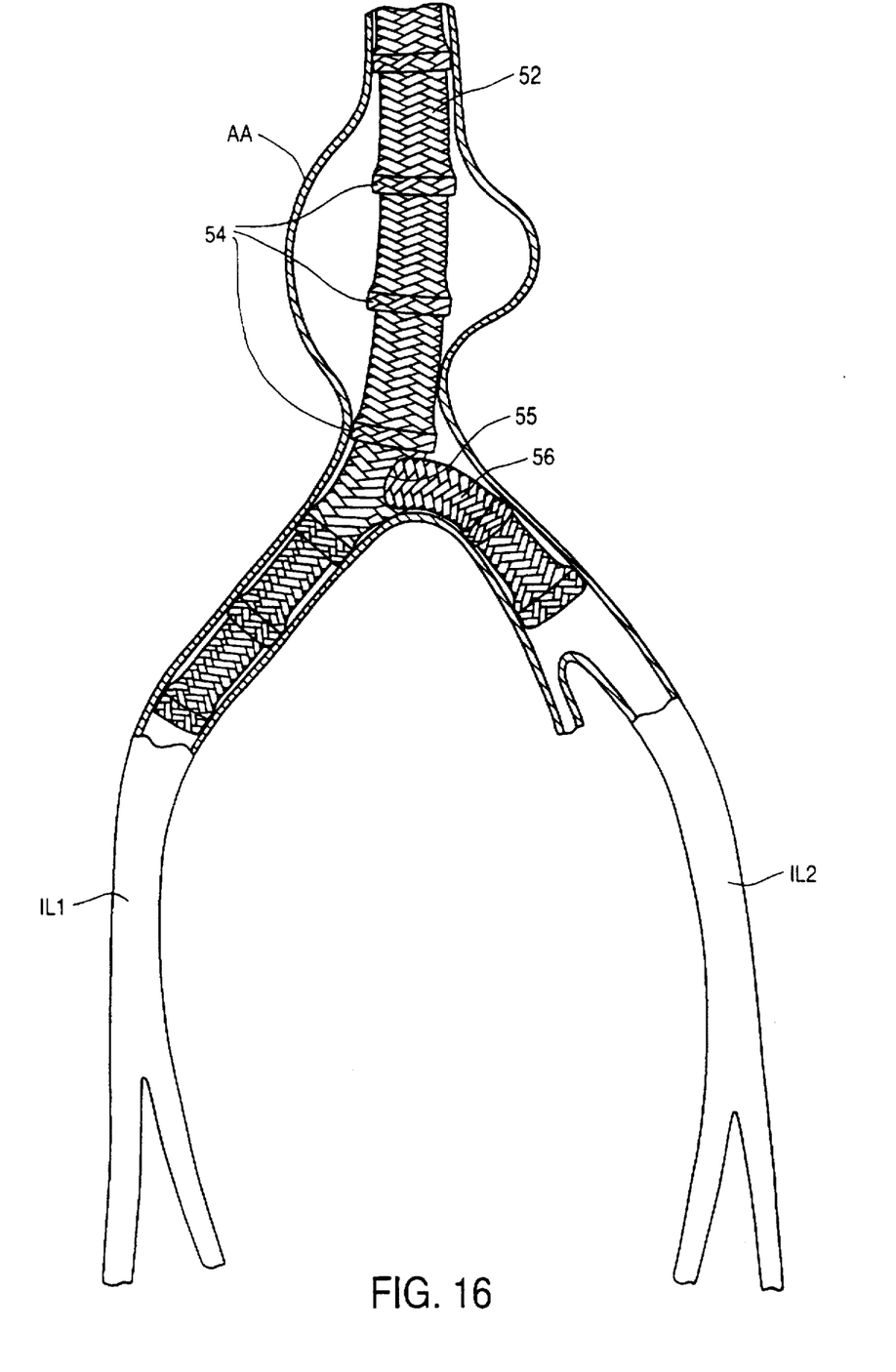

Referring now to FIGS. 14–16, use of the tubular prosthesis 52 of FIGS. 7 and 8 for treatment of an abdominal aortic aneurysm AA in a first technique, the prosthesis 52 in its axially extended configuration (FIG. 7) is introduced to the region of the abdominal aortic aneurysm AA from either a superior or inferior approach. The prosthesis is then axially shortened to cause radial expansion and the formation of multiple eversions 54 to lock the expansion in place. A particular advantage of use of the prosthesis 52 is that the diameter will be supported by the eversions 54 along its entire length. Additionally, the presence of the multiple eversions 54 helps assure good radially outward contact between the prosthesis 52 and the blood vessel wall at many points along its length. As shown in FIG. 14, the prosthesis 52 would be directed into the first iliac IL1, thus isolating the second iliac IL2. To provide blood flow into the second iliac IL2, an autogenous vein graft V could be introduced between the iliacs IL1 and IL2.

An alternative approach for providing blood flow into the second iliac IL2 is shown in FIG. 15. There an opening or port 55 is formed in the side wall of the prosthesis 52 to permit the outward flow of blood into the second iliac IL2. The port 55 may be preformed in the wall of the prosthesis 52, in which case the opening could be reinforced with a stent segment, hooks, springs, or other reinforcement members. Alternatively, by employing a prosthesis 52 formed from a penetrable or heat degradable material, the port 55 can be formed after initial placement of the prosthesis 52. This latter approach has the advantage that the port 55 need not be aligned during introduction of the prosthesis 52. A preferred method for post-placement formation of the port 55 is use of an electrosurgical probe to melt a hole in a polymeric prosthesis, e.g. one formed from polyester or PTFE. The port so formed may be self-supporting, or could be reinforced with a stent or other reinforcement element.

Referring now to FIG. 16, the prosthesis 52 having a port 55 may be further modified or reinforced by a separate prothesis segment 56 which may be placed with one end through the port 55. The stent segment 55 could be similar or identical in construction to the prosthesis 52, except that it will usually be shorter since it needs to traverse a shorter distance.

It will be appreciated that the placement of vascular prosthesis according to the methods of FIGS. 14–16 is not limited to prosthesis having multiple eversions, and any of the self-supporting prosthesis of the present invention could be employed. Use of the prosthesis having multiple eversions, however, will generally be preferred since radial support can be provided relatively uniformly along their entire lengths and the expanded radius of such stent is able to conform to a variety of vessel lumen diameters, making transition from the larger diameter aorta into the smaller diameter iliac easier to achieve.

Although the foregoing invention has been described in some detail by way of illustration and example, for purposes of clarity of understanding, it will be obvious that certain changes and modifications may be practiced within the scope of the appended claims.

What is claimed is:

1. A method for implanting a tubular prosthesis in a body lumen, said method comprising:

transluminally positioning the tubular prosthesis of a target location with in the body lumen;

radially expanding the tubular prosthesis to conform to an inner surface of the body lumen; and everting at least a portion of a wall of tubular prosthesis to fix the radially expanded configuration of the prosthesis.

2. A method as in claim 1, wherein the tubular prosthesis is a stent or graft positioned within a blood vessel.

3. A method as in claim 2, wherein the tubular prosthesis is a graft positioned at an aneurysm within an artery.

4. A method as in claim 1, wherein the tubular prosthesis is released to permit radial self-expansion.

5. A method as in claim 1, wherein the radially expanding step comprises applying force to the tubular prosthesis to effect an increase in diameter.

6. A method as in claim 5, wherein the applied force is a radially expansive force.

7. A method as in claim 5, wherein the tubular prosthesis comprises a braided tubular body and the applied force is an axially compressive force.

8. A method as in claim 1, wherein said everting step comprises everting at least one end of the tubular prosthesis.

9. A method as in claim 8, wherein said everting step comprises everting both ends of the tubular prosthesis.

10. A method as in claim 1, wherein said everting step comprises pulling said at least one end inward into a lumen of the prosthesis.

11. A method as in claim 10, wherein the prosthesis is everted about an axial midpoint so that the resulting structure is folded over in two halves.

12. A method as in claim 1, wherein said everting step comprises everting the prosthesis over a fold line defined by circumferential structure on the tubular prosthesis.

13. A method as in claim 12, wherein the circumferential structure is a weakened line circumscribing the prosthesis.

14. A method for implanting a braided tubular prosthesis in body lumen, said method comprising:

transluminally positioning the braided tubular prosthesis at an aneurysm within an artery within the body lumen;

axially shortening the braided tubular prosthesis to effect radial expansion; and fixing the radially expanded configuration of the braided tubular prosthesis to itself by immobilizing at least a circumference of the braided tubular prosthesis, wherein the braided tubular prosthesis in the radially expanded configuration isolates the aneurysm from bloodflow through the artery.

15. A method as in claim 14, wherein the braided tubular prosthesis is released to permit axial shortening and radial self-expansion.

16. A method as in claim 14, wherein the axially shortening step comprises applying force to the braided tubular prosthesis to effect a decrease in length and an increase in diameter.

17. A method as in claim 16, wherein applied force is an axially compressive force.

18. A method as in claim 16, wherein the applied force is a radially expansive force.

19. A method for implanting a braided tubular prosthesis in a body lumen, said method comprising:

transluminally positioning the braided tubular prosthesis at a target location within the body lumen;

axially shortening the braided tubular prosthesis to effect radial expansion; and fixing the radially expanded configuration of the prosthesis by immobilizing the braided tubular prosthesis in at least one dimension, wherein said at least one dimension is a circumference, and wherein the circumference is immobilized by everting at least a portion of a wall of the braided tubular prothesis.

20. A method as in claim 19, wherein said everting step comprises everting at least one end of the tubular prosthesis.

21. A method as in claim 20, wherein said everting step comprises everting both ends of the tubular prosthesis.

22. A method as in claim 19, wherein said everting step comprises pulling said at least one end inward into a lumen of the prosthesis.

23. A method as in claim 22, wherein the prosthesis is everted about an axial midpoint so that the resulting structure is folded over in two halves.

24. A method as in claim 19, wherein said everting step comprises everting the prosthesis over a fold line defined by circumferential structure on the tubular prosthesis.

25. A method as in claim 24, wherein the circumferential structure is a weakened line circumscribing the prosthesis.

26. A method for implanting a braided tubular prosthesis in a body lumen, said method comprising:

transluminally positioning the braided tubular prosthesis at target location within the body lumen;

axially shortening the braided tubular prosthesis to effect radial expansion, wherein axial shortening results in a decrease in porosity of a wall of the prosthesis, to a final value below about 5000 ml/min/cm$^2$; and fixing the radially expanded configuration of the prosthesis, wherein the fixing step comprises immobilizing the braided tubular prosthesis in at least one dimension, wherein said at least one dimension is circumference; and wherein the circumference is immobilized by everting at least a portion of a wall of the braided tubular prosthesis.

27. A method as in claim 26, wherein said everting step comprises everting at least one end of the tubular prosthesis.

28. A method as in claim 27, wherein said everting step comprises everting both ends of the tubular prosthesis.

29. A method as in claim 26 wherein said everting step comprises pulling said at least one end inward into a lumen of the prosthesis.

30. A method as in claim 26, wherein said the prosthesis is everted about an axial midpoint so that the resulting structure is folded over in two halves.

31. A method as in claim 26, wherein said everting step comprises everting the prosthesis over a fold line defined by circumferential structure on the tubular prosthesis.

32. A method as in claim 31, wherein the circumferential structure is a weakened line circumscribing the prosthesis.

* * * * *